United States Patent [19]

Dicker

[11] Patent Number: 4,943,648
[45] Date of Patent: Jul. 24, 1990

[54] INITIATORS FOR GROUP TRANFER POLYMERIZATION

[75] Inventor: Ira B. Dicker, Wilmington, Del.

[73] Assignee: E. I. du Pont de Nemours and Company, Wilmington, Del.

[21] Appl. No.: 176,807

[22] Filed: Apr. 1, 1988

[51] Int. Cl.$^5$ .......................... C07F 7/08; C07F 7/10; C07F 7/18

[52] U.S. Cl. .................... 556/470; 556/413; 556/415; 556/416; 556/417; 556/418; 556/440; 556/443; 556/446; 556/445

[58] Field of Search .............. 556/420, 443, 446, 413, 556/415, 416, 417, 418, 440, 445

[56] References Cited

U.S. PATENT DOCUMENTS

| | | | |
|---|---|---|---|
| 4,414,372 | 11/1983 | Farnham et al. | 526/190 |
| 4,417,034 | 11/1983 | Webster | 526/190 |
| 4,448,980 | 5/1984 | Sogah | 556/470 X |
| 4,508,880 | 4/1985 | Webster | 526/190 |
| 4,524,196 | 6/1985 | Farnham et al. | 526/190 |
| 4,581,428 | 4/1986 | Farnham et al. | 526/190 |
| 4,588,795 | 6/1986 | Dicker et al. | 526/192 |
| 4,598,161 | 1/1986 | Farnham et al. | 564/101 |
| 4,605,716 | 8/1986 | Hertler | 526/190 |
| 4,622,372 | 11/1986 | Dicker et al. | 526/190 |
| 4,656,233 | 4/1987 | Hertler et al. | 526/190 |
| 4,659,782 | 4/1987 | Spinelli | 525/293 |
| 4,659,783 | 4/1987 | Spinelli | 525/293 |
| 4,681,918 | 7/1987 | Webster | 525/282 |
| 4,695,607 | 9/1987 | Spinelli | 525/272 |
| 4,711,942 | 12/1987 | Webster | 526/185 |
| 4,732,955 | 3/1988 | Dicker | 526/188 |

OTHER PUBLICATIONS

Webster et al., *J. Amer. Chem. Soc.*, 105, 5706 (1983).
Razuvaev et al., *Vysokomol. Soedin.* (B), 25(2): 122–125 (1983).
Sakurai et al., *Tetrahedron Lett.*, 21:2325–2328 (1980).
Burlachenko et al., *Zhur, Obshchei Khim.*, 43 (8), 1724–1732 (1973).
Litvinova et al., abstract of *Dokl. Akad. Nauk., SSSR*, 173, (3): 578–580 (1967) CA 67: 32720.
Baukov et al., abstract of *Dokl. Akad. Nauk., SSSR*, 157 (1): 119–120 (1964); CA B1: 8333(f).
Satchell et al., *Qtr. Rev. Chem. Soc.*, 25, 171 (1971).
Saigo et al., *Chem. Letters*, 2, 163, (1976).

*Primary Examiner*—Paul E. Shaver

[57] ABSTRACT

Process for preparing a silyl ketene acetal adduct, the process comprising contacting and reacting a silyl ketene acetal and an α,β-unsaturated compound in the presence of a mercury- or Lewis acid-containing catalyst, for example, $HgI_2$.

21 Claims, No Drawings

INITIATORS FOR GROUP TRANSFER POLYMERIZATION

BACKGROUND OF THE INVENTION

1. Field of the Invention

This invention relates to the preparation of initiators for Group Transfer Polymerization.

2. Background

U.S. Pat. Nos. 4,414,372; 4,417,034; 4,508,880; 4,524,196; 4,581,428; 4,588,795; 4,598,161; 4,605,716, 4,622,372; 4,656,233; 4,659,782; 4,659,783; 4,681,918; 4,695,607; 4,711,942; and 4,732,955; and in commonly assigned United States Patent Applications Ser. Nos. 912,117 filed Sept. 29, 1986; 934,826 filed Nov. 25, 1986; 004,831 filed Jan. 13, 1987; 007,758 filed Jan. 27, 1987; 015,727 filed Feb. 27, 1987; and 048,958 filed May 19, 1987; referred to hereinafter as "the aforesaid patents and patent applications", disclose processes for polymerizing an acrylic or maleimide monomer to a "living" polymer in the presence of:

(i) an initiator which is a tetracoordinate organosilicon, organotin or organogermanium compound having at least one initiating site; and (ii) a co-catalyst which is a source of fluoride, bifluoride, cyanide or azide ions or a suitable Lewis acid, Lewis base or selected oxyanion. Such polymerization processes have become known in the art as Group Transfer Polymerization (Webster et al., *J. Am. Chem. Soc.*, 105: 5706 (1983)).

Preferred monomers for use in Group Transfer Polymerization are selected from acrylic and maleimide monomers of the formula $CH_2=C(Y)X$ and

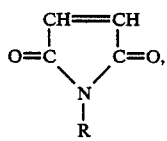

and mixtures thereof,
wherein:

X is —CN, —CH=CHC(O)X' or —C(O)X';

Y is —H, —CH$_3$, —CN or —CO$_2$R, provided, however, when X is —CH=CHC(O)X', Y is —H or —CH$_3$;

X' is —OSi(R$^1$)$_3$, —R, —OR or —NR'R";

each R$^1$, independently, is a hydrocarbyl radical which is an aliphatic, alicyclic, aromatic or mixed aliphatic-aromatic radical containing up to 20 carbon atoms or —H, provided that at least one R$^1$ group is not —H; R is:

(a) a hydrocarbyl radical which is an aliphatic, alicyclic, aromatic or mixed aliphatic-aromatic radical containing up to 20 carbon atoms;

(b) a polymeric radical containing at least 20 carbon atoms;

(c) a radical of (a) or (b) containing one or more ether oxygen atoms within aliphatic segments thereof;

(d) a radical of (a), (b) or (c) containing one or more functional substituents that are unreactive under polymerizing conditions; or (e) a radical of (a), (b), (c) or (d) containing one or more reactive substituents of the formula —Z'(O)—C—C(Y$^1$)=CH$_2$ wherein Y$^1$ is —H or —CH$_3$ and Z' is O or NR40 wherein R' is as defined below; and each of R' and R" is independently selected from C$_{1-4}$ alkyl.

Preferred initiators are selected from tetracoordinate organosilicon, organotin and organogermanium compounds of the formulas (Q')$_3$MZ, (Q')$_2$M(Z$^1$)$_2$ and [Z$^1$(Q')$_2$M]$_2$O wherein:

each Q$^1$, independently, is selected from R$^1$, OR$^1$, SR$^1$ and N(R$^1$)$_2$;

R$^1$ is as defined above for the monomer;

Z is an activating substituent selected from the group consisting of

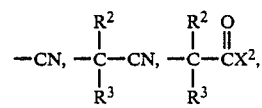

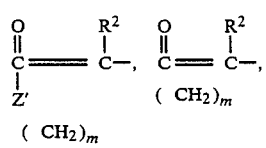

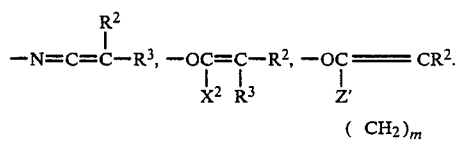

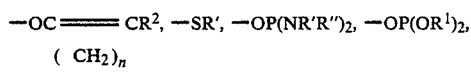

—OP[OSi(R$^1$)$_3$]$_2$ and mixtures thereof;

R',R", R and R$^1$ are as defined above for the monomer;

Z$^1$ is

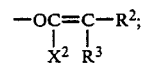

X$^2$ is —OSi(R$^1$)$_3$, —R$^6$, —OR$^6$ or —NR'R";

R$^6$ is (a) a hydrocarbyl radical which is an aliphatic, alicyclic, aromatic or mixed aliphatic-aromatic radical containing up to 20 carbon atoms;

(b) a polymeric radical containing at least 20 carbon atoms;

(c) a radical of (a) or (b) containing one or more ether oxygen atoms within aliphatic segments thereof;

(d) a radical of (a), (b) or (c) containing one or more functional substituents that are unreactive under polymerizing conditions; or (e) a radical of (a), (b), (c) or (d) containing one or more initiating sites; and each of R$^2$ and R$^3$ is independently selected from —H and hydrocarbyl, defined as for R$^6$ above, subparagraphs (a) to (e);

R', R" and R$^1$ are as defined above for the monomer;

Z' is as defined above for the monomer;

m is 2, 3 or 4;

n is 3, 4 or 5;

R$^2$ and R$^3$ taken together are provided Z is

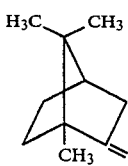

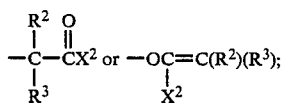

$X^2$ and either $R^2$ or $R^3$ taken together are

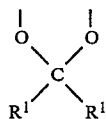

provided Z is

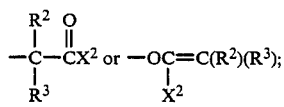

and

M is Si, Sn, or Ge, provided, however, when Z is

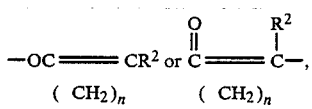

M is Sn or Ge.

Preferred co-catalysts are selected from a source of bifluoride ions $HF_2^-$, or a source of fluoride, cyanide or azide ions, or a source of oxyanions, and oxyanions being capable of forming a conjugate acid having a pKa (DMSO) of about 5 to about 24, preferably about 6 to about 21, more preferably 8 to 18, or a suitable Lewis acid, for example, zinc chloride, bromide or iodide, boron trifluoride, an alkylaluminum oxide or an alkylaluminum chloride, or a selected Lewis base.

Additional details regarding Group Transfer Polymerization can be obtained from the aforesaid patents and patent applications, the disclosures of which are hereby incorporated by reference.

Razuvaev et al., *Vysokomol.Soedin.(B)*, 25(2): 122–125 (1983) disclose polymerization of methyl methacrylate and/or styrene initiated by a mixture of silicon tetrachloride and alkyls of mercury, tin or lead, at 20°–50° C. Sakurai et al, *Tetrahedron Lett.*, 21:2325–2328 (1980) disclose mercuric iodide catalyzed isomerization of (trimethylsilylmethyl)chloromethyl ketone to (1-chloromethyl ethenyl)oxytrimethylsilane.

Burlachenko et al., *Zhur, Obshchei Khim.*,43(8):17-24-1732 (1973) disclose isomerization of cis-ketene silyl acetals into the trans-isomer catalyzed by triethylsilyl bromide and mercuric bromide. Litvinova et al., abstract of *Dokl. Akad. Nauk SSSR*, 173(3):578–580 (1967); CA 67: 32720j, disclose the mercuric iodide-catalyzed rearrangement of triethylacetonylsilane to (isopropenyloxy)triethylsilane.

Baukov et al., abstract of *Dokl. Akad Nauk. SSSR*, 157(1, :119–121 (1964, CA 61: 8333f, disclose the mercuric iodide-catalyzed rearrangement of [(1-methoxy-1-ethenyl)oxy]triethylsilane to methyl 2-triethylsilylacetate.

Satchell et al., *Qtr. Rev. Chem Soc.*, 25:171 (1971) disclose that mercuric halides are very weakly acidic Lewis acids.

Saigo et al.,Chem. Letters, 2, 163 (1976) disclose the Michael-type addition of O-silylated ketene acetals to $\alpha,\beta$-unsaturated carbonyl compounds, specifically ketones and acetals, in the presence of titanium tetrachloride to form 1:1 adducts which are ketoesters.

U.S. Pat. No. 4,732,955, supra, discloses Group Transfer Polymerization of one or more acrylate or acrylamide monomers in the presence of a mercury compound of the formula $R^7HgI$, wherein $R^7$ is a $C_{1-10}$ hydrocarbyl radical, or $HgL_2$, wherein L is I or $ClO_4$. Commonly assigned United States Patent Application Ser. No. 07/176,808 filed Apr. 1, 1988 concurrently filed herewith discloses the use of these mercury compounds in admixture with a silane of the formula $(R^1)_3Si$—$Z^2$ as catalysts in Group Transfer Polymerization. In the formula:

each $R^1$, independently, is a hydrocarbyl radical which is an aliphatic, alicyclic, aromatic or mixed aliphatic-aromatic radical containing up to 20 carbon atoms or —H, provided that at least one $R^1$ group is not —H; and $Z^2$ is I, Br, Cl or trifluoromethylsulfonate.

The present invention provides a process for preparing a 1:1 adduct of a silyl ketene acetal and an $\alpha,\beta$-unsaturated compound, the adduct being an active initiator in Group Transfer Polymerization, the process being catalyzed by a mercury compound or a selected Lewis acid in the presence of a selected silane promoter. There is no suggestion of such a process in any of the foregoing publications. Similar adducts have been prepared using Lewis acid catalysts alone, such as titanium halides, but these reactions require low ($-78°$ C.) temperatures and give poor yields of adduct. With the catalysts used herein, the adduct can be prepared at room temperature, frequently in quantitative yield, and the catalyst residues are readily separated from the reaction mixture.

SUMMARY OF THE INVENTION

The present invention resides in a process for preparing a Group Transfer Polymerization (GTP) initiator which is a silyl ketene acetal adduct (3), the process comprising contacting under reaction conditions a silyl ketene acetal (1) and an $\alpha,\beta$-unsaturated compound (2) in the presence of a catalyst according to the equation:

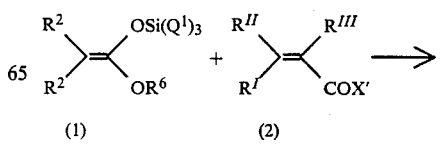

-continued

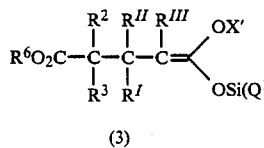

(3)

wherein:

each $Q^1$, independently, is $R^1$ or $OR^1$;

X' is $-OSi(R^1)_3$, $-R$, $-OR$ or $-NR'R''$;

each $R^1$, independently, is a hydrocarbyl radical which is an aliphatic, alicyclic, aromatic or mixed aliphatic-aromatic radical containing up to 20 carbon atoms or $-H$, provided that at least one $R^1$ group is not $-H$;

$R^6$ is (a) a hydrocarbyl radical which is an aliphatic, alicyclic, aromatic or mixed aliphatic-aromatic radical containing up to 20 carbon atoms;

(b) a polymeric radical containing at least 20 carbon atoms;

(c) a radical of (a) or (b) containing one or more ether oxygen atoms within aliphatic segments thereof; or (d) a radical of (a), (b) or (c) containing one or more functional substituents that are unreactive under the process conditions; each of $R^2$ and $R^3$ is independently selected from $-H$ and hydrocarbyl, defined as for $R^6$ above, subparagraphs (a) to (d);

each of $R^I$ and $R_{II}$, independently, is defined as for $R^2$ and $R^3$;

$R^{III}$ is $-CH_3$, $-CN$ or $-CO_2R$; $R^6$ and $R^3$ taken together complete a 5- to 7-membered enyloxy ring;

R is (a) a hydrocarbyl radical which is an aliphatic, alicyclic, aromatic or mixed aliphatic- aromatic radical containing up to 20 carbon atoms;

(b) a polymeric radical containing at least 20 carbon atoms;

(c) a radical of (a) or (b) containing one or more ether oxygen atoms within aliphatic segments thereof;

(d) a radical of (a), (b) or (c) containing one or more functional substituents that are unreactive under the process conditions;

(e) a radical of (a), (b), (c) or (d) containing one or more reactive substituents of the formula $-O(O)C-C(Y^1)=CH_2$ wherein $Y^1$ is $-H$ or $-CH_3$; or (f) a radical of (a), (b), (c), (d) or (e) wherein one or more of the hydrogen atoms is replaced with fluorine atoms; and each of R' and R'' is independently selected from $C_{1-4}$ alkyl; provided, however, when $R^{III}$ is other than $-CH_3$, at least one of $R^I$ and $R^{II}$ is not $-H$.

The catalyst which is essential to the process of the invention consists essentially of either:

(a) (i) about 0.5–100 mole % of a mercury compound selected from $R^7HgI$ and $Hg(L)_2$ wherein:

$R^7$ is a hydrocarbyl radical of 1 to 10 carbon atoms; and

L is an anion, for example, I, Br, Cl, $ClO_4$, $SO_4$, $CF_3SO_3$, $CF_3CO_2$ or O, preferably I or Br, more preferably I; and (ii) 0 to about 99.5 mole % of a silane of the formula $(R^1)_3SiZ^2$ wherein R is defined as above and $Z^2$ is a weakly basic radical, for example, I, Br, Cl, $CF_3SO_3$, $CF_3CO_2$ or $ClO_4$, or (b) (i) about 0.5–90 mole % of a suitable Lewis acid, for example, a zinc (iodide, chloride or bromide), boron trifluoride, an alkyl-aluminum (oxide or chloride), cadmium iodide, ferric chloride or stannous chloride; and (ii) about 10–99.5 mole % of a silane of the formula $(R^1)_3SiZ^2$ wherein $R^1$ is defined as above and $Z^2$ is a weakly basic radical, for example, I, Br, Cl, $CF_3SO_3$, $CF_3CO_2$ or $ClO_4$, provided, however (1) when the catalyst contains 100% of (a)(i), the mercury compound is selected from $R^7HgI$, $HgI_2$ and $Hg(ClO_4)_2$;

(2) when the catalyst is (a), at least one of L and $Z^2$ must be I; and (3) when the catalyst is (a) and $Z^2$ is not I, L is I or $ClO_4$.

DETAILED DESCRIPTION OF THE INVENTION

Preferred silyl ketene acetals (1) for use in the present invention are those wherein $R^1$ and $R^3$ are methyl, $R^2$ is H or methyl and $R^6$ is $C_{1-4}$ alkyl. Preferred $\alpha,\beta$-unsaturated compounds (2) are those wherein, independently, each $R^I$ and $R^{II}$ is H or methyl, $R^{III}$ is methyl, X' is $-OR$ and R is $C_{1-12}$ alkyl, $C_{1-12}$ alkyl wherein some of the H atoms are replaced with F, or $C_{1-12}$ alkyl containing at least one reactive substituent defined as for R, subparagraph (e) above. Bis-monomers wherein R is as defined in subparagraph (e), that is, it contains one reactive substituent, are particularly preferred.

Other than as specified for R, substituents which are reactive under the reaction conditions of the process of this invention or under the polymerization conditions of Group Transfer Polymerization should be avoided unless chemically protected to render them unreactive. Reactive substituents are generally those which react with Lewis acids; examples include OH, $NH_2$, NHR' and $N(R')_2$ wherein R' is alkyl, SH, oxirane and acetals.

The process of the invention is preferably carried out without a solvent. However, solvents which are non-coordinating liquids, such as hydrocarbons or chlorinated hydrocarbons, may be used. For example, toluene, hexane and methylene chloride are satisfactory solvents. Polar solvents, such as ethers, amides and sulfoxides, may prove unsuitable. When a solvent is employed, the concentrations of the reactants are not critical as long as they are dissolved or adequately dispersed. Precautions against hydroxylated impurities, such as water or alcohols, should be observed, as described in the aforesaid patents and patent applications.

The process of the invention should employ at least one mole of silyl ketene acetal (SKA) per mole of $\alpha,\beta$-unsaturated compound, preferably at least two moles. Formation of higher oligomers can be avoided almost completely by the use of excess SKA.

The catalyst is used at a concentration of about 0.1 mole percent to 100 mole percent of the $\alpha,\beta$-unsaturated compound, preferably about 5 to about 30 mole percent of the $\alpha,\beta$-unsaturated compound.

Preferred Lewis acids are zinc halides, more preferably zinc iodide. Preferred silanes are halosilanes (I, Br or Cl), more preferably an iodosilane, most preferably iodotrimethylsilane. As shown in Example 7 hereinafter, zinc halides can catalyze adduct formation at room temperature in the absence of silane promoter, but the reaction is slow and incomplete. Silane promoter is necessary for adduct formation with other Lewis acids of the invention. Mercury compounds of the invention are effective in the absence of silane, but their action is substantially enhanced by the addition of silane. Mixtures with silane are especially useful when it is desired to minimize the amount of mercury or Lewis acid employed in the adduct-forming process.

The process of the invention is operable in the temperature range of about 0° C. to about 100° C., but temperatures of about 15° C. to about 40° C. are preferred. Pressures of atmospheric or higher are preferred, but reduced pressures can be employed, if desired.

The silyl ketene acetals, $\alpha,\beta$-unsaturated compounds and catalysts employed in the process of the invention are known or obvious compounds.

In a preferred embodiment of the invention, a hydrocarbon, such as hexane, is added at the end of the reaction (or as a reaction solvent) to selectively extract the adduct product and excess SKA from insoluble higher oligomers, if any, and residual catalyst.

The 1:1 adducts, of formula 3, which are produced in the process of the invention are themselves silyl ketene acetals and are initiators for Group Transfer Polymerization (GTP) which is discussed in greater detail in the aforesaid patents and patent applications, the disclosures of which are incorporated herein by reference. It is to be understood that the starting SKA compounds used in the process of the invention are also GTP initiators. However, the adducts 3 are generally obtained in higher purity and, as GTP initiators, often provide superior control of molecular weight and enhanced "livingness". Functionalized and bis-initiators prepared by the present process are especially useful for preparing commercially desirable polymers by GTP.

In the following examples of the invention, weight and number average molecular weights of the polymer products ($\overline{M}_w$, $\overline{M}_n$) were measured by gel permeation chromatography (GPC). The polydispersity of the polymer is defined by $D = \overline{M}_w/\overline{M}_n$. Unless otherwise specified, the "living" polymer products were quenched by exposure to moist air or methanol before molecular weights were determined. Differential scanning calorimetry (DSC) was used to measure glass transition temperature of the products. Parts and percentages are by weight and temperatures are in degrees Celsius unless otherwise specified.

Most preferred embodiments of the present invention are represented by Examples 1–4 and 7.

EXAMPLE 1

A. Reaction of [(1-Methoxy-2 methyl-1-propenyl)-oxy]trimethylsilane (MTS) and Methyl Methacrylate To a dry 250-mL round bottom (RB) flask was added 1.0 mL of methyl methacrylate (MMA) (9.3 mmoles), 5.5 mL of MTS (27.5 mmoles) and 0.5 g of $HgI_2$ (1.1 mmole, 4 mole % of MTS). The mixture was stirred under argon for one day, then 100 mL of petroleum ether was added and the mixture was filtered under argon. The pet. ether was removed under reduced pressure and the residue was left on high vacuum for two days (90% yld.). $^1$H NMR: 55:45 mixture of E/Z isomers in benzene ($d_6$):

|  |  | Z | E |
|---|---|---|---|
| (A) Me\C/Me(A) / \CO_2Me(D) CH_2 OMe(C) \/ CH_3 OSiMe_3 (B) | SiMe_3 | 0.154 | 0.142 |
|  | Me(A) | 1.264 | 1.278 |
|  | Me(B) | 1.594 | 1.666 |
|  | CH_2 | 2.472 | 2.400 |
|  | OMe(C) | 3.233 | 3.289 |
|  | OMe(D) | 3.387 | 3.387 |

C and H calc'd.: C 56.93, H 9.49
 found: C 56.73, H 9.27

C and H calc'd.: C 56.93, H 9.49, found: C 56.73, H 9.27

B. Polymerization of MMA

To 30 mL of dry tetrahydrofuran (THF) was added 0.20 mL (0.19 g, 0.69 mmole) of the adduct prepared in Part A. To the solution was added 0.5 mL of 0.01 M tetrabutylammonium bi-benzoate followed by 5.0 mL of MMA added at the rate of 1.0 mL/min. The reaction temperature rose to 36.8° and subsided. One and a half hours from the addition of the MMA an aliquot was withdrawn for GPC analysis (1) and then 5.0 mL more of MMA was added. The mixture temperature again rose, to 42.4°. The next day the polymer (2) was quenched with methanol and precipitated in hexane to give 9.6 g of PMMA (100% of theory).

| (1) | $\overline{M}_n/D$ | 7370/1.12; | $\overline{M}_n$ theory: | 6953 |
| (2) | $\overline{M}_n/D$ | 15700/1.15; | $\overline{M}_n$ theory: | 13706 |

EXAMPLE 2

A. Reaction of MTS with Ethyleneglycol Dimethacrylate

To a 500-mL RB flask were added 2.35 mL of ethyleneglycol dimethacrylate (12.5 mmoles), 10.0 mL of MTS (50 mmoles) and 1.0 g of $HgI_2$ (2.2 mmoles, 4 mole % of MTS). After five days, 100 mL of pet. ether was added and the mixture was allowed to settle. The upper soluble layer was removed and stripped under vacuum, the residual MTS being removed by treatment under high vacuum for three days. Yield: 6.76 g (100%). $^1$H NMR (Benzene($d_6$)): 0.180, 0.197, 0.200, 0.211 (SiMe$_3$); 1.290 (S) 1.298 (S), 1.327 (S), 1.623 (S): 1.635 (S); 1.735 (S); 1.739 (S); 2.407 (S); 2.414 (S); 2.552 (S); 2.587 (S); 3.416 (S); 3.422 (S); 3.428 (S); 3.792 (S); 3.809–3.831 (m); 3.864 (S).

B. Polymerization of MMA

To a 500-mL 3L RB flask under argon containing 225 mL of THF, 0.32 mL (0.32 g, 0.59 mmole) of the bis-initiator product of Part A and 0.12 mL of 0.01 M tetrabutylammonium bi-benzoate was added 75.0 mL of MMA over 2.5 h. Additional catalyst was added (total amount equaled 1.2 mL) to increase the polymerization rate. The maximum temperature reached during the experiment was 34.8°. The next day, the polymerization was quenched with methanol and precipitated in hexane to give a quantitative yield of PMMA. $\overline{M}_n$ 123,000, D = 1.23, $\overline{M}_n$ (theory) 120,000.

EXAMPLE 3

A. Addition of MTS to Telomer 2,6 Methacrylate

To a dry 500-mL RB flask was added 4.00 mL of (2-perfluorohexyl)ethyl methacrylate (Telomer 2,6 methacrylate, 14.8 mmoles), 3.60 mL of MTS (18.0 mmoles) and 1.0 g of $HgI_2$ (2.2 mmoles, 12 mole % of the MTS). After stirring for two days, 300 mL of hexane was added and the supernatant was transferred to a new flask. The hexane was stripped off on a rotovap at 30°, then the remaining volatiles were removed under high vacuum for three days to give 3.18 g (35% yield) of fluorinated adduct initiator. $^1H$ NMR [benzene $(d_6)$]: 52:48 mixture of E/Z isomers

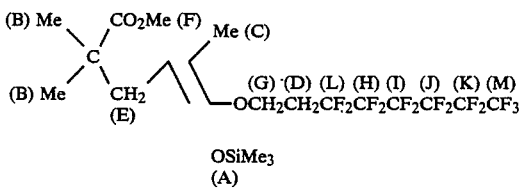

A: 0.151, 0.174; B: 1.279, 1.293; C: 1.601, 1.662; D: 2.02–2.33 (m); E: 2.371, 2.476; F: 3.420, 3.423; G: 3.813 (t,J=6.2 Hz) and 3.881 (t,J=6.2 Hz). $F^{19}$ NMR [benzene $(d_6)$+fluorotrichloromethane] H: −126.3; I: −123.6; J: −123; K: −122; L: −113; M: −81.2 (t,J=9.6 Hz).

B. Polymerization of MMA

To 30 mL of THF was added 0.6 mL of the fluorinated adduct initiator prepared in Part A (0.99 mmole) and 0.30 mL of 0.01 M tetrabutylammonium bi-benzoate. After five minutes, 5.0 mL of MMA was added over five minutes, whereupon the mixture heated exothermically. After precipitation in hexane, 3.45 g (66% yield) of PMMA was obtained. $\overline{M}_n$ 6290, D=1.09, $\overline{M}_n$ (theory) 5240. $F^{19}$ NMR $(CDCl_3)$ confirmed the presence of the fluorinated end-group: −114, −122.4, −123.4, −124.4, −126 6, −81.3 $(CF_3)$.

EXAMPLE 4

A. Addition of MTS to Trimethanolpropanetrimethacrylate

To a dry 500-mL RB flask was added 2.0 mL of trimethanolpropanetrimethacrylate (5.9 mmoles), 6.60 mL of MTS (33 mmoles), 10.0 mL of dry toluene and 1.0 g of $HgI_2$. After stirring for two days, 300 mL of hexane was added and the supernatant liquor was transferred to a new flask. The hexane was stripped off on a rotovap at 30' and then the remaining volatiles were removed under high vacuum over three days to give 4.31 g (88% yield) of the adduct tris-initiator. $^1H$ NMR was consistent with the assigned structure.

B. Polymerization of MMA

The procedure of Example 3 was followed, using 1.0 ml (1.2 mmole) of the tris-initiator prepared in Part A instead of the fluorinated initiator, to give a quantitative yield of PMMA. $\overline{M}_n$ 4500, D=1.52, $\overline{M}_n$ (theory) 4681.

EXAMPLE 5

Addition of Z/E [(1 methoxy 1 propenyl)oxy]-trimethyl-silane to MMA

To an NMR tube was added 1 mL of benzene $(d_6)$ saturated with $HgI_2$, 0.1 mL of Z/E [(1-methoxy-1-propenyl)oxy]trimethylsilane (0.54 mmole) and 56 mL of MMA (0.60 mmole). After one day, analysis indicated the absence of residual MMA and the $^1H$ NMR spectrum was consistent with the formation of the 1:1 adduct.

EXAMPLE 6

Addition of MTS to Methyl Crotonate

The procedure of Example 5 was followed except that 0.1 mL of MTS and 53 μL of methyl crotonate were used. After one day, the methyl crotonate was consumed and the $^1H$ NMR spectrum was consistent with the formation of the 1:1 adduct.

EXAMPLE 7

Addition of MTS to Ethylene Glycol Dimethacrylate

A. To a dry 25 mL round bottom flask containing 0.17 g (0.53 mmole) of zinc iodide and a stir bar was added 2.0 mL of ethylene glycol dimethacrylate (10.6 mmoles) and 6.4 mL (30 mmoles) of MTS. The mixture was stirred and then 0.15 mL (1.0 mmole) of iodotrimethylsilane was added. The temperature rose After about 2 h, NMR analysis showed only the product bis-initiator and unreacted excess MTS; all the starting dimethacrylate had reacted. Stripping off volatiles at 0.01 mm (1.3 Pa) gave a quantitative yield of the bis-initiator which was then dissolved in benzene, filtered through Celite ™, and then re-stripped. The final oil was shown to initiate Group Transfer Polymerization of MMA with tetrabutylammonium bibenzoate as catalyst.

B. The procedure of Part A was repeated except that iodotrimethylsilane was omitted. Product work-up and analysis showed that, after 2 h, only 53% of the ethylene glycol dimethacrylate had been consumed.

EXAMPLE 8

To an NMR tube was added 0.60 mL of a 0.003 M solution of mercuric iodide in benzene $(d_6)$, 0.1 mL of methyl methacrylate, 0.37 mL of MTS initiator, and 0.030 mL of trimethylsilyliodide. Concentrations of mercuric iodide, trimethylsilyliodide and MMA in the final solution were $1.68 \times 10^{-3}$ M, 0.19 M, and 0.87 M, respectively. Dimer formation occurred within 5 min, confirmed by NMR analysis.

The above experiment was repeated but in the absence of trimethylsilyliodide; dimer formation proceeded very slowly to 50% conversion after 21 hours. The experiment was again repeated but in the absence of mercuric iodide; no dimer formation was observed.

I claim:

1. Process for preparing a silyl ketene acetal adduct, the process comprising contacting and reacting a silyl ketene acetal and an α,β-unsaturated compound in the presence of a mercury- or Lewis acid-containing catalyst, A. the silyl ketene acetal being of the formula

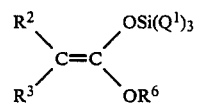

wherein:
$R^6$ is
(a) a hydrocarbyl radical which is an aliphatic, alicyclic, aromatic or mixed aliphaticaromatic radical containing up to 20 carbon atoms;
(b) a polymeric radical containing at least 20 carbon atoms;

(c) a radical of (a) or (b) containing one or more ether oxygen atoms within aliphatic segments thereof; or (d) a radical of (a), (b), or (c) containing one or more functional substituents that are unreactive under the process conditions;

each of $R^2$ and $R^3$ is independently selected from —H and hydrocarbyl, defined as for $R^6$ above, subparagraphs (a) to (d);

each $Q^1$, independently, is $R^1$ or $OR^1$;

each $R^1$, independently, is a hydrocarbyl radical which is an aliphatic, alicyclic, aromatic or mixed aliphatic-aromatic radical containing up to 20 carbon atoms or —H, provided that at least one $R^1$ group is not —H;

B. the α,β-unsaturated compound being of the formula

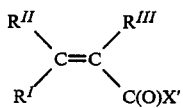

wherein:

each of $R^I$ and $R^{II}$, independently, is as defined for $R^2$ and $R^3$ above;

$R^{III}$ is —$CH_3$, —CN or —$CO_2R$;

X' is —$OSi(R^1)_3$, —R, —OR or —NR'R";

R is (a) a hydrocarbyl radical which is an aliphatic, alicyclic, aromatic or mixed aliphaticaromatic radical containing up to 20 carbon atoms;

(b) a polymeric radical containing at least 20 carbon atoms;

(c) a radical of (a) or (b) containing one or more ether oxygen atoms within aliphatic segments thereof;

(d) a radical of (a), (b) or (c) containing one or more functional substituents that are unreactive under the process conditions;

(e) a radical of (a), (b), (c) or (d) containing one or more reactive substituents of the formula —O(O)C—C($Y^1$)=$CH_2$ wherein $Y^1$ is —H or —$CH_3$; or (f) a radical of (a), (b), (c), (d), or (e) wherein at least some of the hydrogen atoms are replaced with fluorine atoms; and each of R' and R" is independently selected from $C_{1-4}$ alkyl; and C. the catalyst consists essentially of either:

(a) (i) about 0.5-100 mole % of a mercury compound selected from $R^7HgI$ and $Hg(L)_2$ wherein:
$R^7$ is a hydrocarbyl radical of 1 to 10 carbon atoms; and
L is an anion; and (ii) 0 to about 99.5 mole % of a silane of the formula $(R^1)_3SiZ^2$ wherein $R^1$ is defined as above and $Z^2$ is a weakly basic radical; or (b) (i) about 0.5-90 mole % of a Lewis acid selected from zinc iodide, zinc chloride, zinc bromide, boron trifluoride, alkyl-aluminum oxide, alkyl-aluminum chloride, cadmium iodide, ferric chloride and stannous chloride; and (ii) about 10-99.5 mole % of a silane of the formula $(R^1)_3SiZ^2$ wherein $R^1$ is defined as above and $Z^2$ is a weakly basic radical; provided, however:

(1) when the catalyst contains 100% of (a)(i), the mercury compound is selected from $R^7HgI$, $HgI_2$ and $Hg(ClO_4)_2$;

(2) when the catalyst is (a), at least one of L and $Z^2$ must be I; and (3) when the catalyst is (a) and $Z^2$ is not I, L is I or $ClO_4$.

2. Process of claim 1 wherein the catalyst contains a mercury compound.

3. Process of claim 1 wherein

A. in the formula for the silyl ketene acetal: each of $R^1$ and $R^3$ is methyl; $R^2$ is H or methyl; and $R^6$ is $C_{1-4}$ alkyl; and B. in the formula for the α,β-unsaturated compound:
each of $R^I$ and $R^{II}$, independently, is H or methyl;
$R^{III}$ is methyl;
X' is OR; and
R is $C_{1-12}$ alkyl, $C_{1-12}$ alkyl wherein one or more of the H atoms is replaced with F, or $C_{1-12}$ alkyl containing one or more reactive substituents of the formula —O(O)C—C($Y^1$)=$CH_2$ wherein $Y^1$ is —H or —$CH_3$.

4. Process of claim 1 wherein the molar ratio of A to B is at least one.

5. Process of claim 1 wherein the molar ratio of A to B is at least two.

6. Process of claim 1 wherein the amount of C is about 0.1-100 mole % of the amount of B.

7. Process of claim 1 wherein the amount of C is about 5-30 mole % of the amount of B.

8. Process of claim 1 wherein the reaction temperature is about 0°-100° C.

9. Process of claim 1 wherein the reaction temperature is about 15°-40° C.

10. Process of claim 1 carried out in the presence of a solvent.

11. Process of claim 1 carried out in the presence of a non-coordinating solvent.

12. Process of claim 2 wherein the mercury compound is mercuric iodide.

13. Process of claim 1 wherein $Z_2$ in the silane is selected from I, Br, Cl, $CF_3SO_3$, $CF_3CO_2$ and $ClO_4$.

14. Process of claim 13 wherein the silane is iodotrimethylsilane.

15. Process of claim 3 wherein R is $C_{1-12}$ alkyl containing one or more reactive substituents.

16. Process of claim 15 wherein R contains 2 to 4 carbon atoms.

17. Process of claim 3 wherein R is $C_{1-12}$ alkyl wherein one or more H atoms is replaced with a F atom.

18. Process of claim 17 wherein R is 2-perfluorohexylethyl.

19. Process of claim 1 wherein the catalyst contains a Lewis acid.

20. Process of claim 19 wherein the Lewis acid is selected from zinc iodide, zinc chloride and zinc bromide and the silane is a halide.

21. Process of claim 20 wherein the Lewis acid is zinc iodide and the silane is iodotrimethylsilane.

* * * * *